United States Patent [19]
Arai

[11] Patent Number: 6,111,259
[45] Date of Patent: Aug. 29, 2000

[54] COLOR ADJUSTING METHOD

[75] Inventor: Yujin Arai, Akiruno, Japan

[73] Assignee: Olympus Optical Co., Ltd., Tokyo, Japan

[21] Appl. No.: 09/153,780

[22] Filed: Sep. 15, 1998

[30] Foreign Application Priority Data

Sep. 18, 1997 [JP] Japan .................................. 9-253428

[51] Int. Cl.$^7$ ................................................ G01N 21/64
[52] U.S. Cl. .................................. 250/459.1; 250/458.1; 250/461.1; 250/461.2; 250/492.2
[58] Field of Search ........................... 250/459.1, 458.1, 250/492.2, 461.1, 461.2

[56] References Cited

U.S. PATENT DOCUMENTS 5,866,911  2/1999  Baer ..................................... 250/458.1
6,043,506  3/2000  Heffelfinger et al. .................. 250/584

FOREIGN PATENT DOCUMENTS 5-183739  7/1993  Japan .
8-163387  6/1996  Japan .

OTHER PUBLICATIONS

Y. Miyake; "Topics of Color Reproduction for Non–Impact Printings"; 1995; pp. 826–831; Bulletin of Society of Television Technology, vol. 49, No. . 7.

*Primary Examiner*—Constantine Hannaher
*Assistant Examiner*—Otilia Gabor
*Attorney, Agent, or Firm*—Frishauf, Holtz, Goodman, Langer & Chick, P.C.

[57] ABSTRACT

A color chart where hue and saturation are changed variously with lightness kept constant is outputted onto a CRT monitor (or a color printer) beforehand. The display color corresponding to a specific wavelength of fluorescence in visual observation is specified on the color chart. The hue and saturation for the display color at that time are stored as color conversion parameters in a data processing unit. Thereafter, the color tone of the one with a specific wavelength of fluorescence among the luminance data of fluorescence of the observed specimen is corrected using the color conversion parameters. The resulting observed image is outputted to the CRT monitor (or color printer). This enables color reproduction of the observed image easily.

15 Claims, 3 Drawing Sheets

COLOR ADJUSTING METHOD

BACKGROUND OF THE INVENTION

The present invention relates to a color adjusting method for an observed image from a laser scanning microscope, for example.

Fluorescence microscopes have been known as instruments used to observe a fluorescent image of an observed specimen. In the fluorescence microscope, a specimen to be observed is dyed beforehand with a fluorescent reagent that generates fluorescence when receiving light with a specific wavelength. Illumination light with the specific wavelength is introduced via an objective. The fluorescence generated at the specimen is observed with the naked eye via the objective. The observed image may be recorded by photography.

Since it is very difficult to meet exposure requirements for photographing a fluorescent image of the observed specimen in the best condition, it is difficult to obtain a good picture. Since the result of photographing is known only after development, a failure in the photography will be known later, if any. This worsens the working efficiency significantly.

To overcome this problem, instead of such a fluorescence microscope, use of a laser scanning microscope where illumination light has been replaced with laser light has been considered. Specifically, in the laser scanning microscope, a laser light serving as a point source is projected via an objective on a specimen, while being caused to scan the specimen in the direction of the x-axis and that of the y-axis. A sensor senses the florescence from the specimen via the objective and the optical system, and produces a two-dimensional luminance data. The two-dimensional distribution of the luminance data is displayed on an image output unit, such as a CRT monitor or a color printer, in such a manner that the two-dimensional distribution comes to correspond to the x-y scanning position. This visualizes the observed image and enables the user to look at it. Such a laser scanning microscope visualizes the observed image more easily and accurately than the aforementioned fluorescence microscope.

Laser scanning microscopes further include a confocal laser scanning microscope equipped with a confocal optical system which is capable of sensing only data on the surface in focus by providing with a stop with a diameter equal to or less than the diffraction limit of the illumination light or the light to be measured in a position conjugate to the specimen, obtaining data items on the surface in focus at each position on Z-axis, and thereby producing a three-dimensional image.

The laser scanning microscopes have been treated as sophisticated measuring instruments capable of measuring two-dimensional or three-dimensional fluorescence images with high sensitivity and high resolution. As electronic imaging technology, data processing technology, and multimedia technology have recently made rapid progress, they have begun to be used as means for observing a fluorescent specimen as ordinary fluorescence microscopes are.

As such a laser scanning microscope is used as means for observing a fluorescent specimen, accurate data on colors which has not been regarded as very important have come to be needed.

Since conventional laser scanning microscopes is configured to obtain luminance data of two-dimensional or three-dimensional fluorescence and is not capable of obtaining data on colors of fluorescence, they adopt a method of directly displaying the luminance data of fluorescence as the luminance data of image or displaying pseudo colors by applying a suitable color for each luminance level, thereby causing to be easy to distinguish the subtle differences in the density which have been difficult to distinguish visually. However, such a method is not enough to obtain accurate data on colors.

To bring the data as close to the fluorescence color of the observed object as possible, a method of reproducing color data on the observed specimen by manipulating the RGB three primary colors using a simple look-up table (LUT) has been considered. Specifically, to reproduce color data using such an LUT, a recommended value for each wavelength of fluorescence is set beforehand in the LUT and the color data is reproduced in accordance with the wavelength of fluorescence of the observed specimen. Furthermore, the RGB three primary colors are adjusted subtly so that the reproduced color data may be displayed in the form the operator wants.

With such a method, the hue looks differently from when the fluorescent specimen is observed with the naked eye, depending on the output unit for displaying the observed specimen. In most cases, the hue when the observed image is displayed on a CRT monitor differs from that when the observed image is printed on a color printer. To adjust the colors between those output units so that they may coincide with each other by manipulating the LUT of the RGB three primary colors each time a difference in hue has been found, a certain level of skill and complicated work are needed.

Among these color adjusting techniques, the generally used techniques have confronted the subject of how to reproduce the same color tone when the image on a CRT monitor is printed on a printer, especially how to improve the color reproduction. One method of solving the problem is a method of using software to do complex matrix computation, as disclosed in, for example, Jpn. Pat. Appln. KOKAI Publication No. 8-163387. Another method of solving the problem is a method of using a dedicated circuit to do the matrix computation, as disclosed in Jpn. Pat. Appln. KOKAI Publication No. 5-183789.

These methods have the following problems: since they target the color space transformation in a very wide color gamut like a television dealing with general images, doing complex calculations by software takes an extremely long time and the necessity of providing a complex dedicated circuit for each output unit with a different characteristic results in a rise in production cost.

BRIEF SUMMARY OF THE INVENTION

Accordingly, it is an object of the present invention to provide a color adjusting method capable of reproducing colors of the observed image easily.

According to one aspect of the present invention, there is provided a color adjusting method for use in an image processing unit which measures luminance data of fluorescence of an observed specimen with a laser scanning microscope and outputs an observed image to an output unit based on the luminance data, the method comprising the steps of: outputting to the output unit a color chart where hue and saturation are changed variously with lightness kept constant; specifying on the color chart a display color which corresponds to a specific wavelength of fluorescence in visual observation and storing the hue and saturation corresponding to the display color as color conversion parameters; and correcting a color tone of the one with the specific wavelength of fluorescence among the luminance data of fluorescence of the observed specimen measured with the laser scanning microscope, and outputting a resulting observed image to the output unit.

In the method, it is desirable that the color tone correction is executed such that the hue and saturation represented by the color conversion parameters corresponding to the specific wavelength of fluorescence are outputted and the lightness corresponding to the luminance data of fluorescence at that time is outputted.

In the method, it is desirable that the color conversion parameters are set for each output unit with a different display characteristic and stored.

In the method, as a relationship between the luminance data of fluorescence measured with the laser scanning microscope and the lightness of the observed image of the output unit, the decrease of the lightness may be suppressed in the region where the luminance data of fluorescence is smaller and the increase of the lightness may be suppressed in the region where the luminance data of fluorescence is larger.

In the method, it is desirable that the display color is specified using a pointing device or a keyboard.

In the method, the color chart may have hue on its abscissa and saturation on its ordinate.

In the method, the output unit may include a display unit. In this case, it is desirable that, on the screen of the display unit, the observed image obtained from the laser scanning microscope may be displayed with the color chart such that the observed image is colored with the display color specified on the color chart.

In the method, the output unit may include a color printer. In this case, the color chart outputted on the color printer may be graduated in coordinates so that the display color can arbitrarily specified on the color chart. The hue and saturation corresponding onto a coordinate position of the display color specified on the color chart may be stored as the color conversion parameters. Also, an upper limit and a lower limit may be set on a region where the lightness of the observed image to be outputted to the color printer is applied.

In the method, the observed image obtained from the color tone correction may be converted into RGB data and outputted to the output unit. Alternatively, the observed data obtained from the color tone correction may be converted into CMY(K) data and outputted to the output unit.

According to another aspect of the present invention, there is provided an image processing unit which measures luminance data of fluorescence of an observed specimen with a laser scanning microscope and outputs an observed image to an output unit based on the luminance data, the image processing unit comprising: means for outputting to the output unit a color chart where hue and saturation are changed variously with lightness kept constant; means for storing as color conversion parameters the hue and saturation corresponding to a display color which has been arbitrarily specified on the color chart, the specified display color corresponding to a specific wavelength of fluorescence in visual observation; and means for correcting a color tone of the one with the specific wavelength of fluorescence among the luminance data of fluorescence of the observed specimen measured with the laser scanning microscope, and outputting a resulting observed image to the output unit.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention in which.

DETAILED DESCRIPTION OF THE INVENTION

Hereinafter, referring to the accompanying drawings, embodiments of the present invention will be explained.

(First Embodiment)

Figure 1:
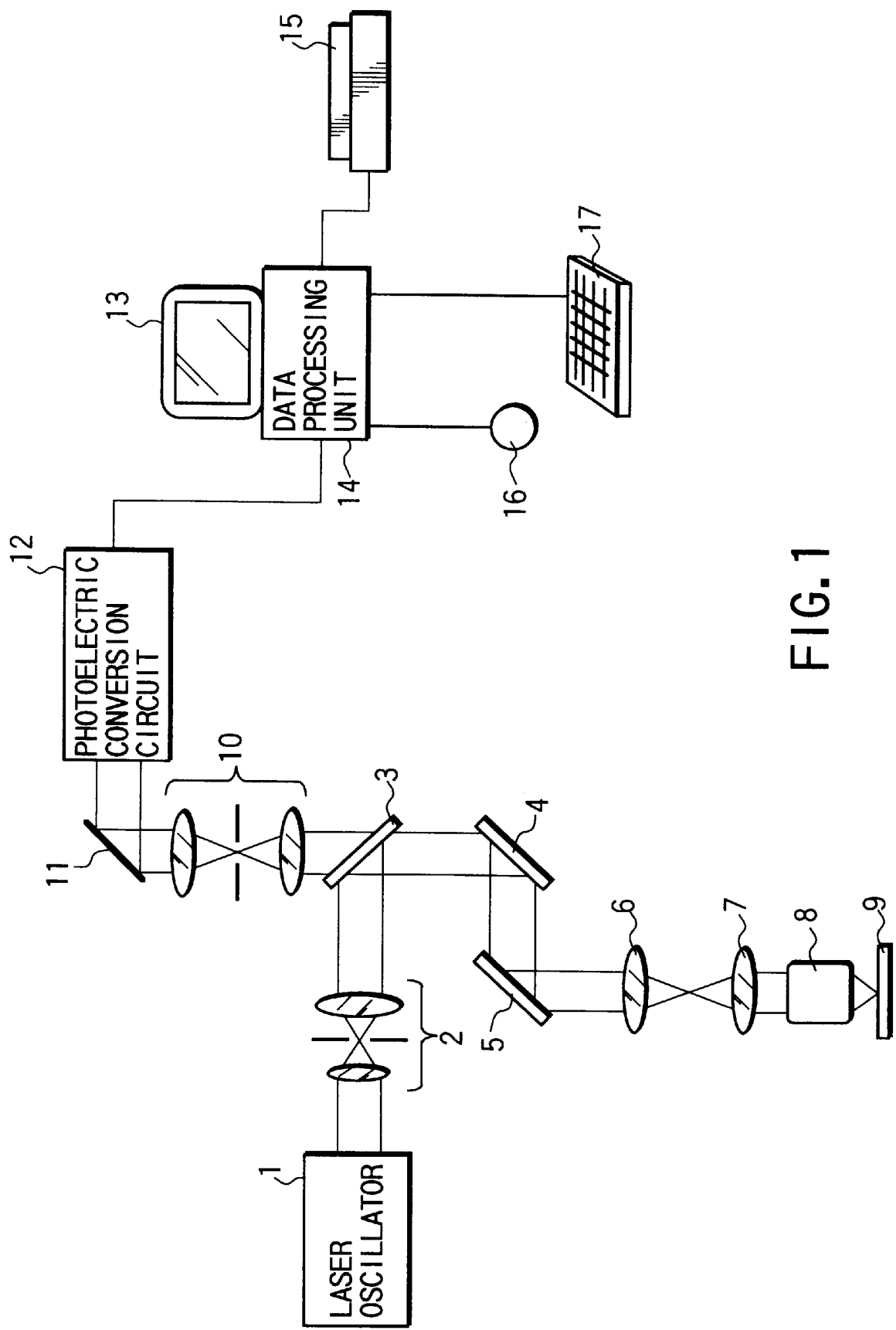
FIG. 1 shows a schematic configuration of a confocal laser scanning microscope to which a color adjusting method according to a first embodiment of the present invention is applied.

FIG. 1 shows a schematic configuration of a confocal laser scanning microscope to which a color adjusting method of the present invention is applied.

The confocal laser scanning microscope includes a laser oscillator 1 acting as a light source, a beam expander 2, an optical path dividing element 3, an x-direction scanner 4, a y-direction scanner 5, an eye projection lens 6, a condense lens 7, an objective 8, a specimen 9, a confocal optical system 10, a wavelength selecting element 11, a photoelectric conversion circuit 12, a data processing unit 13, a display unit (CRT monitor) 14, and a color printer 15.

The laser light emitted from the laser oscillator 1 passes through the beam expander 2 and the optical path dividing element 3, such as a beam splitter or a dichroic mirror, and enters the x-direction scanner 4 and y-direction scanner 5. The x-direction scanner 4 and y-direction scanner 5 constitute a galvanometer scanner. The laser light entering the x-direction scanner 4 and that entering y-direction scanner 5 are deflected so as to effect two-dimensional scanning.

The laser light emitted from the y-direction scanner 5 passes through the eye projection lens 6, condense lens 7, and objective 8, and is scanned on the specimen 9 two-dimensionally. Subsequently, the fluorescence from the specimen 9 travels along the same optical path as that of the incident laser light in the opposite direction and reaches the optical dividing element 3. The light then penetrates through the optical path dividing element 3, passes through the confocal optical system 10 including a pinhole, and the wavelength selecting element 11 composed of a dichroic mirror and an interference filter, and is directed as luminance data on the fluorescence to the photoelectric conversion circuit 12. While only one photoelectric conversion circuit is used for clarity, more than one wavelength selecting element and photoelectric conversion circuit may be used. Namely, the present invention may be applied to a case where more than one wavelength of fluorescence is measured.

After the luminance data on the fluorescence converted by the photoelectric conversion circuit 12 into an electric signal has been subjected to various processes at the data processing unit 13, the resulting signal is displayed as an observed image on the output unit, such as the CRT monitor 14 or the color printer 15.

In this case, because the wavelength selecting element 11 allows only a single wavelength of the fluorescence to enter the photoelectric conversion circuit 12, the output data from the photoelectric conversion circuit 12 represents luminance for each wavelength (color) of fluorescence.

The following is an explanation of color adjustment in the output units, such as the CRT monitor 14 or color printer 15, that display the observed image with such a confocal laser scanning microscope.

To specify colors in an image output unit, it is a common practice to represent colors using the ratio and density of the RGB three primary colors. Since in this method it is difficult to change the brightness while keeping the color tone constant, a method of representing colors using hue (H), saturation (S), and lightness (I) is adopted in this embodiment.

Figure 2:
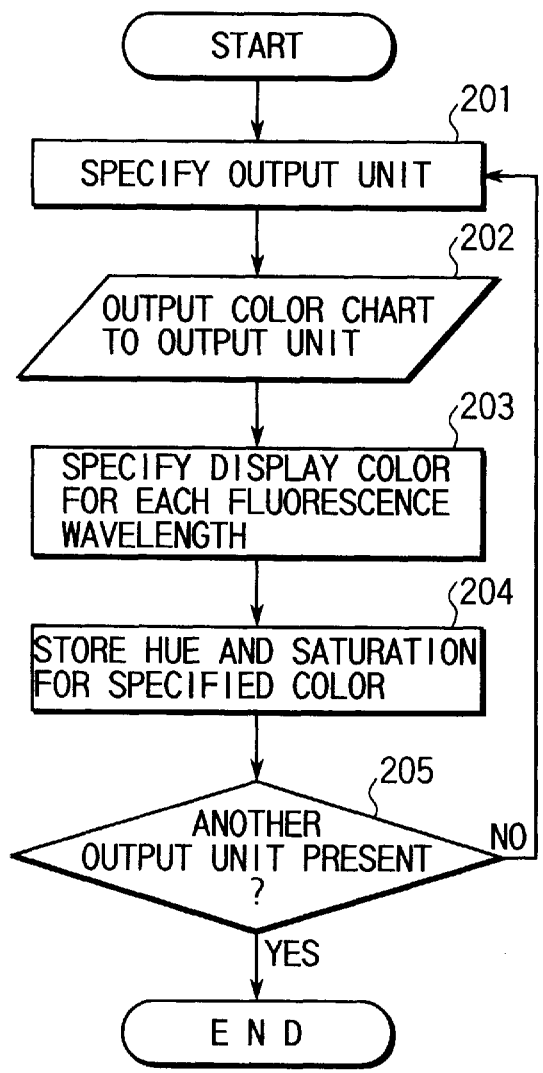
FIG. 2 is a flowchart to help explain the procedure for setting color conversion parameters in the first embodiment.

The color conversion parameters are set according to the flowchart of FIG. 2.

In this case, at step 201, an output unit to which the observed image is to be outputted is specified on the basis of an output unit list (not shown) stored in the data processing unit 13. In the example shown, either the CRT monitor 14 or the color printer 15 is specified. Here, the CRT monitor 14 is assumed to have been specified.

Figure 3:
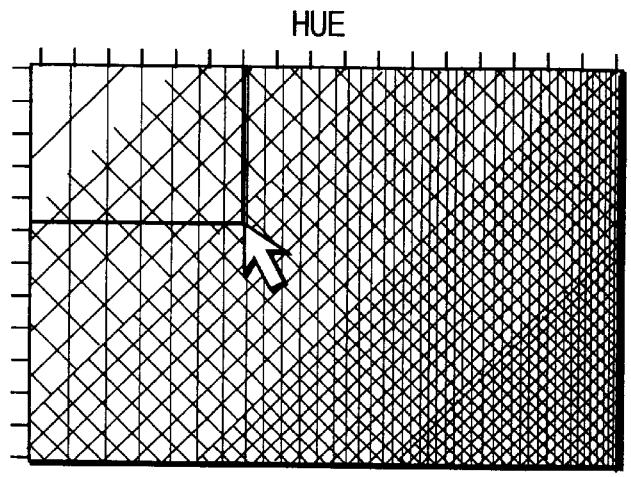
FIG. 3 shows a color chart used in setting color conversion parameters in the first embodiment.

Next, at step 202, a color chart is displayed on the screen of the specified CRT monitor 14 as shown in FIG. 3. In the color chart, hue is taken on the abscissa and saturation is taken on the ordinate and the hue and saturation are changed variously with the lightness kept constant. It is desirable that the lightness of the displayed color chart at that time should be about ½ of the maximum lightness.

Then, at step 203, the display color corresponding to a specific wavelength of fluorescence in actual visual observation is selected from the display colors in the color chart on the CRT monitor 14, using the input unit 16, such as a pointing device (a mouse, a light pen, or a tablet) connected to the data processing unit 13. Specifying a display color on the color chart is effected for the other wavelengths of fluorescence in the same manner. Instead of the input unit 16, the input unit (an accupoint or a track pad) provided on the data processing unit 13 may be used.

When the actually observed image on the specimen 9 is displayed with the color chart on the screen of the CRT monitor 14 in such a manner that the data is colored in accordance with the parameters for hue and saturation specified on the color chart, it can be determined whether the data corresponds to the specific wavelength of fluorescence in visual observation. This makes it easier to select the parameters for hue and saturation.

Then, at step 204, the hue and saturation corresponding to the display color specified on the color chart of the CRT monitor 14 are stored as color conversion parameters into the data processing unit 13.

Next, at step 205, it is determined whether another output unit is present. Because the color printer 15 is present, control returns to step 201. The color printer 15 is specified this time and control proceeds to step 202 and later. The color printer 15 prints out a color chart with coordinate axes suitably graduated. The operator reads the coordinates for hue and saturation for each wavelength of fluorescence and enters the coordinate data from the input unit 17, such as a keyboard, connected to the data processing unit 13. The data processing unit 13 then converts the coordinate data into the corresponding parameters for hue and saturation. Instead of the input unit 17, the operator may use an input unit (e.g., a keyboard) provided in the data processing unit 13.

By repeating the processes shown in the flowchart of FIG. 2, color conversion parameters for color adjustment of each wavelength of fluorescence for the CRT monitor 14 and color printer 15 can be acquired.

The following is an explanation of how to display the actually observed image on the CRT monitor 14 or color printer 15 using the acquired color conversion parameters for each of the CRT monitor 14 and color printer 15.

Because in the present invention, a representation based on hue (H), saturation (S), and lightness (I) is used, it is required to convert the hue, saturation, and lightness into RGB (or CMY(K)) data to output the observed image on the output unit such as the CRT monitor 14 or color printer 15. Various conversion methods using color models have been considered. With any of the conversion methods, if the aforementioned color chart output coincides with the actually observed image output, there will be no large visual change in the color tone. Therefore, there is no need to set a limit on a method of transforming the color space.

Figure 4:
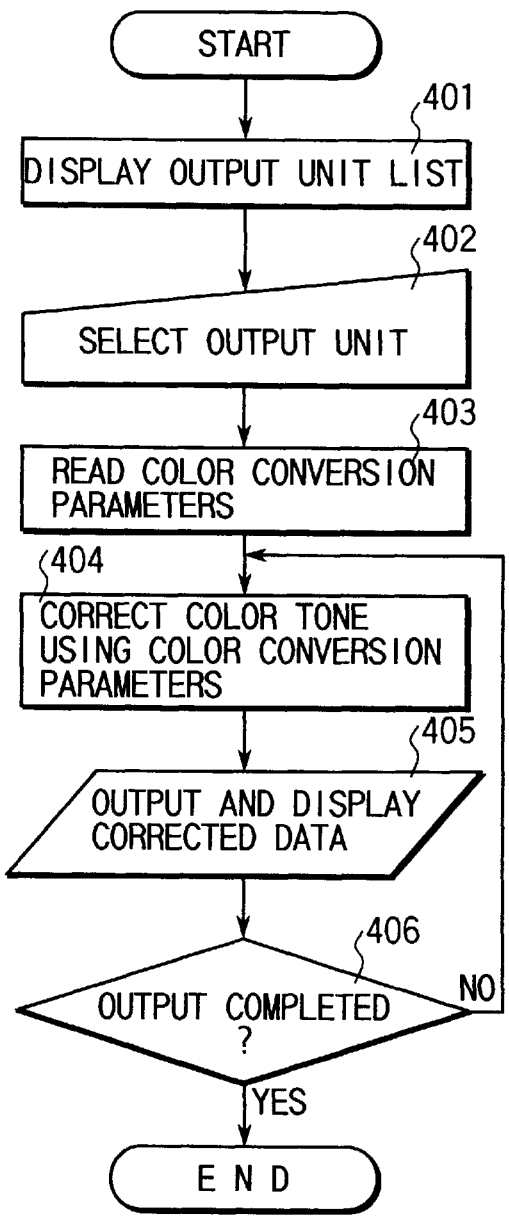
FIG. 4 is a flowchart to help explain the procedure for outputting an observed image in the first embodiment.

After the output of the observed image has been started, the process shown in the flowchart of FIG. 4 is executed.

At step 401, a list of output units is displayed. At step 402, an output unit to which the observed image is to be outputted is specified on the basis of the displayed list. In the example shown, either the CRT monitor 14 or the color printer 15 is specified. Here, the CRT monitor 14 is assumed to have been specified.

At step 403, the data processing unit 13 reads the stored color conversion parameters for each of the wavelengths of fluorescence onto the selected output unit, or the CRT monitor 14.

Then, at step 404, the fluorescent of the specimen 9 is measured with the confocal laser scanning microscope shown in FIG. 1. When the photoelectric conversion circuit 12 outputs luminance data on a specific wavelength of fluorescence after the measurement, the data processing unit 13 uses the fluorescence luminance value as lightness and makes color tone correction of the specified wavelength of fluorescence using color conversion parameters. Specifically, the data processing unit 13 makes color tone correction so that the hue and saturation represented by the color conversion parameters corresponding to the specific wavelength of fluorescence are outputted, and the lightness corresponding to the fluorescence luminance at that time may be outputted, thereby determining hue (H), saturation (S), and lightness (I).

Then, at step 405, the color tone-corrected data is converted into RGB data or CMY (K) data, which is displayed as an observed image on the CRT monitor 14.

The data processing unit 13 also makes color tone correction of luminance data on another wavelength of fluorescence in the same manner using color conversion parameters.

Similarly, in the case of the color printer 15, when the photoelectric conversion circuit 12 has outputted luminance data on the specific wavelength of fluorescence from the specimen 9, the data processing unit 13 uses the luminance data of fluorescence at that time as lightness and makes color tone correction of the specified wavelength of fluorescence using color conversion parameters. The resulting observed image is outputted to the color printer 15.

Then, at step 406, after the output to the CRT monitor 14 or color printer 15 has been completed, the process is terminated.

As described above, a color chart in which the hue and saturation are changed variously with the lightness kept constant are displayed beforehand on the CRT monitor 14 (or the color printer 15). The operator specifies on the color chart a display color corresponding to a specific wavelength of fluorescence in visual observation. The data processing unit 13 stores the hue and saturation for the display color at that time as color conversion parameters. Thereafter, using the color conversion parameters, the data processing unit 13 makes color tone correction of the one with the specific wavelength of fluorescence among the luminance data of fluorescence of the measured specimen 9. This makes it possible to reproduce on the CRT monitor 14 (or color printer 15) an image whose coloring is approximate to that of the fluorescent image in visual observation. Furthermore, accurate data on colors can be collected, enabling high-accuracy fluorescence observation.

Because the setting of color conversion parameters by use of a color chart is effected for each of the CRT monitor 14 and color printer 15, a fluorescent image with almost the same coloring can be reproduced even when either the CRT monitor 14 or color printer 15 is used. Using the observed image outputted from either the CRT monitor 14 or color printer 15 enables high-accuracy fluorescence observation.

While in the embodiment, the CRT monitor 14 and color printer 15 are connected as the output units, the present invention may be applied to a case where more CRT monitors and color printers are connected. Furthermore, other types of display unit, such as a liquid-crystal display, may be used in place of the CRT monitor.

(Second Embodiment)

Figure 5A:
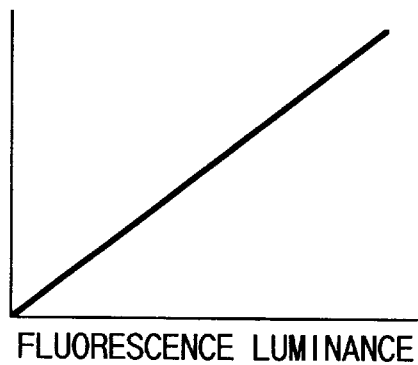
FIGS. 5A to 5C are diagrams to help explain a second embodiment of the present invention.

In the first embodiment, uniform color reproduction has been achieved even with a different output unit for displaying the observed specimen. When the measured values of the fluorescence luminance are allocated linearly as lightness as shown in FIG. 5A after a hue and a saturation have been specified, the portion corresponding to the low fluorescence luminance tends to have low lightness and be colored gray, whereas the portion corresponding to the high fluorescence luminance tends to have high lightness and be colored whitish. As a result, when the sensitivity of the photoelectric conversion circuit 12 is set relatively low and the luminance data of fluorescence is measured, all of the obtained image has a grayish, subdued color. When the sensitivity of the photoelectric conversion circuit 12 is set relatively high, all of the obtained image has a whitish color. Namely, the obtained image differs from the fluorescence image viewed with the naked eye.

Figure 5B:
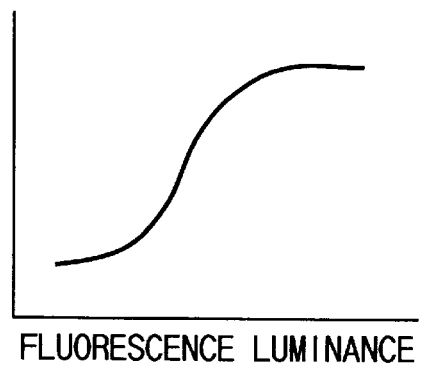

To overcome this problem, as shown in FIG. 5B, the second embodiment of the present invention suppresses not only the decrease of lightness in the region where the measured values of the fluorescence luminance are small but also the increase of lightness in the region where the measured values of the fluorescence luminance are large. With this relationship between the fluorescence luminance and the lightness, the fluorescence luminance is caused to be converted into the lightness.

This assures a constant lightness even when the sensitivity of the photoelectric conversion circuit 12 is set relatively low and the fluorescence luminance is measured. As a result, a gray representation is prevented. Even when the sensitivity of the photoelectric conversion circuit 12 is set high, the lightness will not exceed a specific value, preventing a whitish representation. This makes it possible to reproduce the coloring of the fluorescent image approximate to that of the image observed with the naked eye under the fluorescence microscope.

Figure 5C:
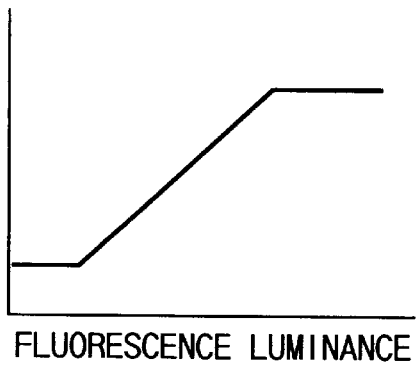

Since the color printer 15 has a narrower color gamut than the CRT monitor 14, the range where lightness is applied to the fluorescence luminance is made narrower as shown in FIG. 5C in the case of the color printer 15. Specifically, an upper limit and a lower limit are set on the region where lightness is applied. This makes it possible to approximate the observed image of the color printer 15 to the observed image of the CRT monitor 14.

As described in detail, with the present invention, the hue and saturation for the display color corresponding to a specific wavelength of fluorescence in visual observation are set as color conversion parameters beforehand using a color chart. Thereafter, using the color conversion parameters, the color tone of the one with the specific wavelength of fluorescence among the luminance data of fluorescence of the measured specimen 9 is corrected. This makes it possible to reproduce on the output unit an image whose coloring is approximate to that of the fluorescent image in visual observation. Furthermore, accurate data on colors can be collected, enabling high-accuracy fluorescence observation.

Because the setting of color conversion parameters by use of a color chart is effected for each output unit, a fluorescent image with almost the same coloring can be reproduced with an output unit having a different display characteristic. Accordingly, even when the output unit is changed, high-accuracy fluorescence observation can be achieved.

Because a specific level of lightness is assured even when the fluorescence luminance value is small and the lightness is prevented from exceeding a specific value even when the fluorescence luminance value is large, this prevents a gray representation or whitish representation of the observed image, which thereby reproduces the coloring of the fluorescent image approximate to that of the image viewed with the naked eye under the fluorescence microscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A color adjusting method for use in an image processing unit which measures luminance data of fluorescence of an observed specimen with a laser scanning microscope and outputs an observed image to an output unit based on the luminance data, said method comprising the steps of:

outputting to said output unit a color chart where hue and saturation are changed variously with lightness kept constant;

specifying on said color chart a display color which corresponds to a specific wavelength of fluorescence in visual observation and storing the hue and saturation corresponding to the display color as color conversion parameters; and correcting a color tone of the displayed color with the specific wavelength of fluorescence among the luminance data of fluorescence of the observed specimen measured with said laser scanning microscope, and outputting a resulting observed image to said output unit.

2. A color adjusting method according to claim 1, wherein said color tone correction is executed such that the hue and saturation represented by the color conversion parameters corresponding to said specific wavelength of fluorescence are outputted and the lightness corresponding to the luminance data of fluorescence at that time is outputted.

3. A color adjusting method according to claim 1, wherein said color conversion parameters are set for each output unit with a different display characteristic and stored.

4. A color adjusting method according to claim 1, wherein as a relationship between the luminance data of fluorescence measured with said laser scanning microscope and the lightness of the observed image of said output unit, the decrease of the lightness is suppressed in the region where the luminance data of fluorescence is smaller and the increase of the lightness is suppressed in the region where the luminance data of fluorescence is larger.

5. A color adjusting method according to claim 1, wherein said display color is specified using a pointing device or a keyboard.

6. A color adjusting method according to claim 1, wherein said color chart has hue on its abscissa and saturation on its ordinate.

7. A color adjusting method according to claim 1, wherein said output unit includes a display unit.

8. A color adjusting method according to claim 7, wherein on the screen of said display unit, the observed image obtained from said laser scanning microscope is displayed with said color chart such that the observed image is colored with the display color specified on the color chart.

9. A color adjusting method according to claim 1, wherein said output unit includes a color printer.

10. A color adjusting method according to claim 9, wherein the color chart outputted on said color printer is graduated in coordinates so that the display color can arbitrarily be specified on the color chart.

11. A color adjusting method according to claim 10, wherein the hue and saturation corresponding onto a coordinate position of the display color specified on said color chart are stored as said color conversion parameters.

12. A color adjusting method according to claim 9, wherein an upper limit and a lower limit are set on a region where the lightness of the observed image to be outputted to said color printer is applied.

13. A color adjusting method according to claim 1, wherein the observed image obtained from said color tone correction is converted into RGB data and outputted to said output unit.

14. A color adjusting method according to claim 1, wherein the observed data obtained from said color tone correction is converted into CMY(K) data and outputted to said output unit.

15. An image processing unit which measures luminance data of fluorescence of an observed specimen with a laser scanning microscope and outputs an observed image to an output unit based on the luminance data, said image processing unit comprising:

means for outputting to said output unit a color chart where hue and saturation are changed variously with lightness kept constant;

means for storing as color conversion parameters the hue and saturation corresponding to a display color which has been arbitrarily specified on said color chart, the specified display color corresponding to a specific wavelength of fluorescence in visual observation; and means for correcting a color tone of the display color with the specific wavelength of fluorescence among the luminance data of fluorescence of the observed specimen measured with said laser scanning microscope, and outputting a resulting observed image to said output unit.

* * * * *